United States Patent [19]

Houghton

[11] Patent Number: 4,866,984

[45] Date of Patent: Sep. 19, 1989

[54] SENSOR AND SYSTEM FOR CONTINUOUS DETERMINATION OF PAPER STRENGTH

[75] Inventor: Paul J. Houghton, Los Gatos, Calif.

[73] Assignee: Measurex Corporation, Cupertino, Calif.

[21] Appl. No.: 195,364

[22] Filed: May 13, 1988

Related U.S. Application Data

[63] Continuation of Ser. No. 887,292, Jul. 18, 1986, abandoned, which is a continuation-in-part of Ser. No. 784,213, Oct. 4, 1985, abandoned.

[51] Int. Cl.⁴ .............................................. G01L 5/04
[52] U.S. Cl. ...................................................... 73/159
[58] Field of Search .................. 73/159, 11, 769, 773, 73/774, 761, 785, 788, 794, 804, 838, 862.48, 862.54, 862.04, 862.07, 862.68, 866; 162/263, 49

[56] References Cited

U.S. PATENT DOCUMENTS

| | | | |
|---|---|---|---|
| 2,674,127 | 4/1954 | Garrett et al. | 73/159 |
| 2,809,519 | 10/1957 | Kaestner | 73/159 |
| 2,826,911 | 3/1958 | Hartford et al. | 73/159 |
| 2,909,660 | 10/1959 | Alexander | 162/263 |
| 2,966,792 | 1/1961 | Ciro de Pieri . | |
| 3,204,454 | 9/1965 | Friman et al. | 73/862.04 |
| 3,474,668 | 10/1969 | Mangan | 73/159 |
| 3,552,203 | 1/1971 | Freeh | 162/263 |
| 3,619,360 | 11/1971 | Persik . | |
| 3,622,448 | 11/1971 | Adams et al. . | |
| 3,711,688 | 1/1973 | Stout et al. . | |
| 3,718,037 | 2/1973 | Stringer et al. . | |
| 3,738,151 | 6/1973 | Giunta et al. | 73/1 B |
| 3,757,122 | 9/1973 | Bossen et al. . | |
| 3,793,878 | 2/1974 | Brunton | 73/88.5 |
| 3,822,588 | 7/1974 | Knight et al. | 73/81 |
| 4,068,385 | 1/1978 | Mitzel | 33/143 |
| 4,080,656 | 3/1978 | Johnsson et al. . | |
| 4,291,577 | 9/1981 | Baum et al. | 73/597 |
| 4,374,703 | 2/1983 | Lebeau et al. . | |
| 4,453,404 | 6/1984 | Powell et al. | 73/159 |
| 4,587,855 | 5/1986 | Yamada et al. | 73/862.48 |
| 4,674,310 | 6/1987 | Ginzberg . | |
| 4,678,915 | 7/1987 | Dahlquist et al. . | |

FOREIGN PATENT DOCUMENTS

| | | |
|---|---|---|
| 751614 | 10/1954 | Fed. Rep. of Germany . |
| 1008503 | 5/1957 | Fed. Rep. of Germany . |
| 1012760 | 7/1957 | Fed. Rep. of Germany . |
| 475609 | 6/1979 | Switzerland . |
| 0934328 | 8/1963 | United Kingdom . |
| 1328158 | 8/1973 | United Kingdom . |

OTHER PUBLICATIONS

A High Temperature Four-Point Bending Machine for Testing Thin Sheets of Refractory Materials, J. L. Martin, R. Case, A. Devacht and P. Costa, Office National D'Etudes et de Recherches Aerospatiales, 12/29/70.
Foxborough Bulletin, Aug. 1964.
Check-Line Type DTM Microprocessor-Controlled Tensiometer Brochure, (no date available).
"On-Line Measurement of Strength of a Moving Sheet", M. T. Lu, TAPPI, vol. 58, No. 6, pp. 80-81, Jun. 1975.
"Control in the Paper Industry Industry up to the Minute", E. J. Kompass, Control Engineering, vol. 25, No. 12, pp. 44-46, Dec. 1978.

Primary Examiner—Stewart J. Levy
Assistant Examiner—Robert R. Raevis
Attorney, Agent, or Firm—Spensley Horn Jubas & Lubitz

[57] ABSTRACT

A sensor for continuous sensing of a quantity of paper related to its elastic modulus and stiffness including a paper support in the form of a segmented ring, and a free running wheel which depresses the paper in the center of the ring as the paper passes over it. Force transducers mounted to sense force exerted on the segments provides a measure of a characteristic of the paper related to its elastic modulus and bending stiffness. The segments are aligned so that separate determinations of machine direction and cross-direction characteristics are made. The outputs of this sensor, together with basis weight, thickness and paper velocity are used to determine the strength of the paper on a continuous basis. Separate values of machine direction and cross-direction strength can be determined, as can a burst pressure strength.

35 Claims, 3 Drawing Sheets

SENSOR AND SYSTEM FOR CONTINUOUS DETERMINATION OF PAPER STRENGTH

REFERENCE TO RELATED APPLICATIONS

This is a continuation of copending application Ser. No. 887,292, filed on July 18, 1986, now abandoned, which is a continuation-in-part of Application Ser. No. 06/784,213 filed Oct. 4, 1985, now abandoned.

BACKGROUND OF THE INVENTION

One of the critical parameters involved in the manufacture of paper is its strength; virtually all paper manufactured is sold with a strength specification of some sort, and acceptance of a manufacturer's paper depends on his being able to meet this requirement. Consequently, it would be desirable to measure paper strength "on line" as it is being manufactured, in order to avoid the production of substandard material. Since papermaking is a high speed continuous process, large amounts of paper can easily be produced before strength can be confirmed by a later measurement.

Two problems which make the measurement of strength "on line" difficult arise from the facts that the strength of paper varies across the width of the sheet being produced, and is also different in the machine direction and the cross sheet direction. The system disclosed in my copending application "Sensor and System for Continuous Determination of Paper Strength" (Ser. No. 06/784/213) is intended to allow a continuous determination of strength and its variation across the width of the sheet. However, the sensor used does not have the capability to separate machine direction strength from cross direction strength and therefore does not provide a complete picture of the characteristics of the paper.

Strength specifications for paper are usually given in terms of an empirical destructive test, the more common of these being a standardized tensile test, the so-called "STFI" compression test, and the "burst pressure" or "Mullen" test.

In the standard tensile test, a strip of paper held between two clamps is loaded in tension at a predetermined rate. The loading at failure is taken to be a measure of the tensile strength of the paper. There are a number of standardized procedures which have been adopted to perform this test, e.g., TAPPI Standard T404os-76 and ASTM Standard D828.

The "STFI" compression test for heavy papers is a standardized test whose procedure has been established by the Swedish Technical Forest Institute, as specified by the identifier: Scan P46 Column 83. In this test a strip of the paper to be tested is held between a pair of clamps which are moved together at a fixed rate while the compressive force is monitored. "Rupture" occurs when the compressive force passes the peak and begins to drop. The force at "rupture" is taken as the compressive strength of the paper. Other standard specifications for this test are, e.g., TAPPI 7818os-76 and ASTM D1164.

The strengths of papers as measured by the foregoing tests typically have different values depending on whether the test strip is cut in the machine direction or the cross direction.

A "Mullen" or burst pressure test is conducted by clamping a sample of the paper between two circular clamping rings having a specified standard inside diameter, and building up pressure on one side of the paper until the paper bursts (using a rubber diaphragm and liquid pressure). The pressure required to burst the paper is known as the "burst pressure" and is the figure often used to specify the required strength. Common burst pressure specifications are TAPPI 403os-76 and ASTM D7774.

Needless to say, none of these tests lend themselves to use in connection with the continuous measurement of paper strength. Because of their widespread popularity, however, any method used to measure the strength of paper should provide results which correlate with one of the recognized standard tests.

SUMMARY OF THE INVENTION

It is an object of the present invention to provide a system for determining the strength of paper being manufactured—on line—where separate determinations of machine direction and cross direction strength can be made and which exhibits good correlation with presently used accepted tests.

By its nature, a measurement of paper strength is destructive. Fortunately, however, I have found that the strength of paper is related to factors which are known, or can be measured on a continuous basis by nondestructive means. The major factors which have been identified as affecting the strength of paper are its "elastic modulus", its basis weight, and its thickness. Quotation marks are used around the term "elastic modulus" to indicate that the function, while related to the elastic modulus is really an empirically derived factor which depends on other characteristics also. The most important secondary factor involved is the bending stiffness of the sheet. In any particular paper making set up, changing the speed of the web also affects the strength of the resulting product.

Elastic modulus and bending stiffness are difficult, if not impossible to measure directly on a moving web of paper. However, in my copending application referred to above, I describe a sensor which can sense a physical manifestation of the paper related to these characteristics and can provide an output which, when taken together with the other aforementioned factors, can be used to determine paper strength continuously and nondestructively. This sensor can provide a measurement which allows a strength determination to be made which correlates well with the popular "Mullen" test. In the present application, a sensor is described which not only allows a Mullen determination to be made but allows separate determinations of machine and cross direction tensile and compressive strengths.

The "elastic modulus" sensor in the presently preferred embodiment of the present invention uses a paper web support ring which is split into four segments, each occupying approximately 90 degrees of the ring circle. Each segment is supported on a pair of leaf springs and a load cell so that force down on the paper in the center of the ring will result in an output from each of the four load cells, with the output level being dependent in part on paper characteristics. The four segments are aligned so that two are sensitive to machine direction characteristics of the paper and two are sensitive to cross direction characteristics. A free running wheel pressing on the paper at the center of the web support ring provides the force which is transmitted to each load cell.

A computer accepts the outputs of each of the load cells, as well as outputs from sensors which sense basis weight, paper thickness, paper velocity and certain correction factors. The computer calculates paper strength using these signals in accordance with certain empirical equations which have been developed.

It should be understood that while references are made to specific standardized tests herein, the references are intended to be exemplary only and not limiting. The present invention can be utilized to provide determinations which correlate well with a wide variety of standardized tensile, compressive and burst pressure tests.

A clear understanding of the invention can be had by referring to the following detailed description of the presently preferred embodiment of the invention together with the appended drawings.

DETAILED DESCRIPTION OF THE INVENTION

Paper is ordinarily made in a continuous sheet by high speed machines, often several hundred feet in length. The process involves laying a wet mass of wood pulp onto a moving wire fabric belt, drying and mass, and finally calendering the sheet to give it the desired surface finish. The present invention is most advantageously used to monitor the strength of the paper after the final calendering operation, and before the paper is rolled up on the final reel. A reroll motor maintains a constant tension in the sheet between the calender and the reroll reel. Since the strength of the paper produced may vary across the sheet as well as along the sheet, the present invention preferably involves the use of a scanning system whereby the sensors scan across the width of the paper while the paper is being fed out of the calender and into the reroll system.

Figure 1:
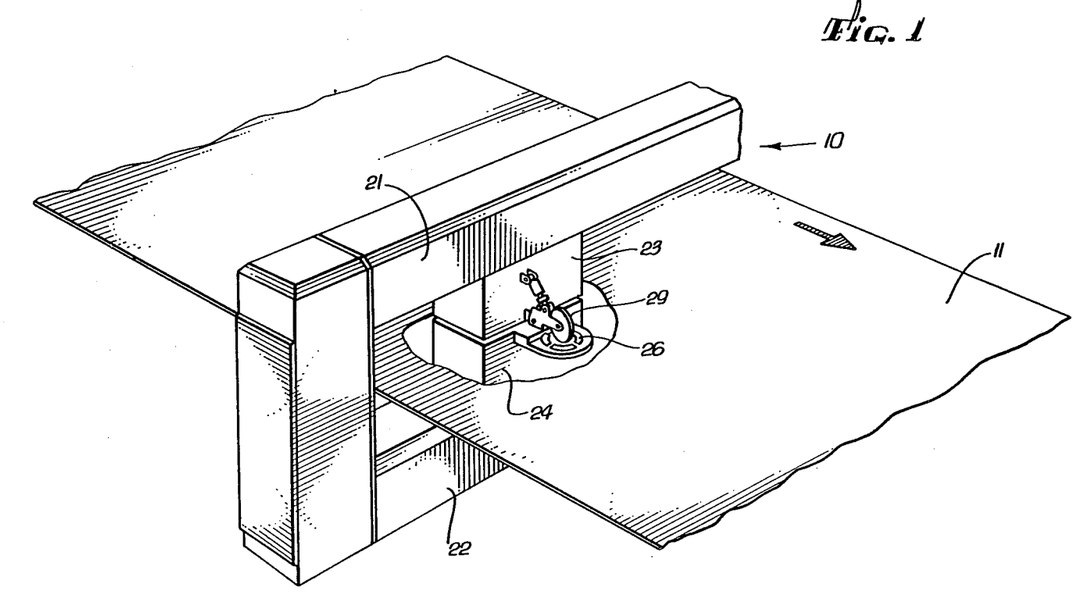
FIG. 1 is a perspective view of the sensing portion of the invented apparatus as installed in a paper making machine.

FIG. 1 shows a scanning station 10 which, as noted above, is preferably located after the final calender rolls and before the reroll system. A web of paper 11 can be seen passing through the scanning station 10 between two transverse beams 21 and 22, on which are mounted upper and lower gage support members 23 and 24. The web of paper 11 in FIG. 1 is shown with a cut out area so that the relationship between the gage support members can be seen. A motor within the scanning station is coupled to, and drives the gage support members 23, 24 back and forth across the width of the paper in a continuous scanning motion, keeping them in alignment at all times.

The gage support members carry four sets of sensors which provide the data used to calculate paper strength. The four factors used are basis weight, thickness, "elastic modulus", and the velocity of the web. Means for determining basis weight, thickness, and paper velocity are all known in the prior art and are therefore not shown on the drawings or discussed individually herein. Thickness and paper velocity are relatively simple to measure, and many methods are known in the prior art. Basis weight is a more complex matter, but a suitable method is disclosed in U.S. Pat. No. 3,757,122 issued to Bossen et al. The fourth sensor provides data which relates to the "elastic modulus" of the paper. As noted above, the "elastic modulus" sensor is responsive not only to the elastic modulus of the sheet, but also to its stiffness in bending.

Figure 2:
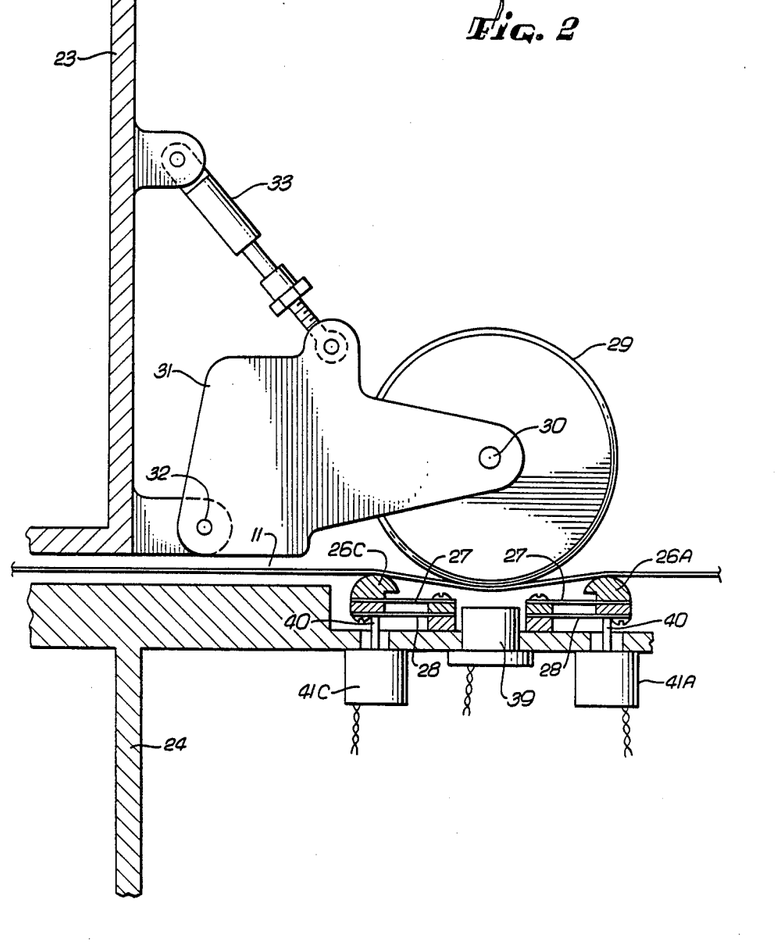
FIG. 2 is a cross-sectional side view of the sensor for sensing the "elastic modulus" of the paper.

FIG. 2 shows a partially sectioned side view of the invented "elastic modulus" sensor. Lower gage support 24 supports a segmented horizontal ring 26A-26D whose top surface is preferably aligned with the paper web 11. While a ring such as ring 26 is the preferred method of support, other forms of supporting structure could be used which support the paper in the vicinity of a central region.

Upper gage support 23 carries the pressure wheel assembly which is comprised of bracket 31 and wheel 29. Pin 32 allows the wheel freedom to move up and down while bearings on axle 30 (not shown) permit the wheel to rotate freely. Up and down motion of the wheel 29 is controlled by air cylinder 33. In its extended position, air cylinder 33 positions the lower portion of the periphery of wheel 29 a fixed distance below the top surface of ring 26. For purposes of example, and not by way of limitation, if the diameters of wheel 29 and ring 26 are each about 5 inches, a satisfactory position for the lowest point on wheel 29 may be ¼ inch below the top surface of ring 26.

Figure 4:
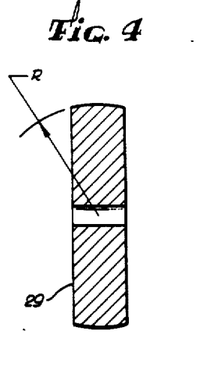
FIG. 4 is a fragmentary cross-sectional view of the sensing wheel.

The periphery of wheel 29 is preferably not cylindrical but, rather, is preferably approximately spherical. That is, the radius R as shown in FIG. 4 is preferably approximately equal to one-half the wheel diameter. Retraction of air cylinder 33 moves wheel 29 out of the way so that a web of paper 11 can be fed through the scanning station easily upon initial set up. During operation, air cylinder 33 is extended.

It will be understood by those skilled in the art that while a free running wheel is disclosed herein for the purpose of deflecting the paper below the top surface of ring 26, other structures can be utilized to accomplish the same function.

Figure 3:
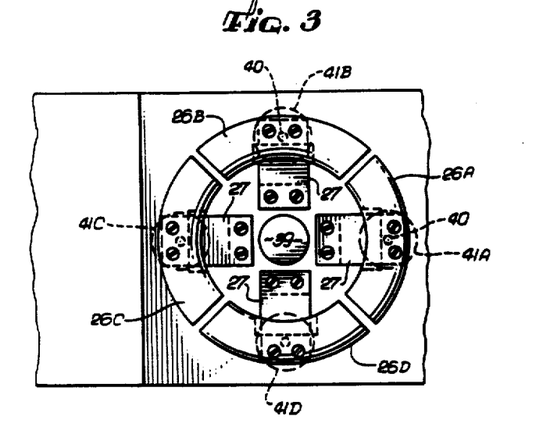
FIG. 3 is a top plan view of the portion of the lower gage support member in the region of the sensing ring.

FIG. 3 is a top plan view of the portion of the lower gage support member which supports the segmented ring 26. Referring both FIGS. 2 and 3, it can be seen that the ring 26 is comprised of four segments, 26A-26D which are each supported by a pair of spaced leaf springs 27 and 28. The leaf springs 27, 28 constrain the segments 26A-D to move with straight line vertical motion. Linkage pins 40 couple each segment to load cells 41A-41D which provide outputs that are a function of the paper force on the ring segments. The force exerted on each of the segments 26 is a function of several factors including the tension on the sheet, the elastic modulus of the paper, the bending stiffness of the paper, and the physical dimensions of the gaging components. The modulus of elasticity and the bending stiffness of the paper may be different in the machine direction as compared to the width direction, so that the force applied to load cells 41A and 41C is not necessarily the same as the force applied to load cells 41B and 41D. I have found that there is a correlation between the force applied to the load cells 41A and 41C and the machine direction strength of the paper and also a correlation between the force applied to load cells 41B and 41D and the cross-direction strength of the paper.

Figure 5:
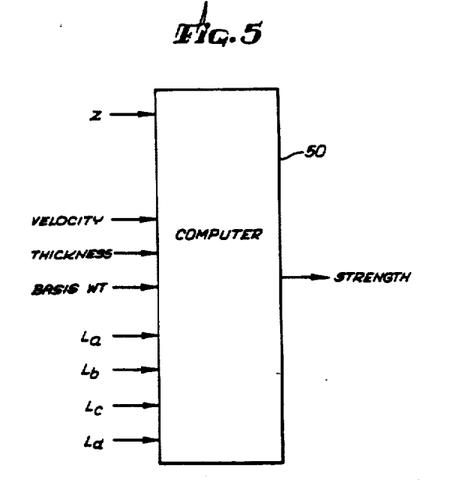
FIG. 5 is a block diagram of the electronic portion of the invention.

In order to make a strength determination, the outputs of transducers 41A-D are fed to a computer 50 which also receives signals from the other sensors referred to above. The computer 50, by repeated calculations, provides continuous determinations of the strength of the paper as it is being manufactured. Empirical equations have been developed which correlate well with standard machine direction and cross direction strength tests as well as with the nondirectional standard burst pressure or "Mullen" test.

The accuracy of the basic equations developed depends upon keeping the alignment of the top surface of ring 26 even with the web of paper 11 as it is being fed into or out of the scanning station 10. If the incoming web 11 is higher or lower than the top surface of ring 26, a correction to the basic equation must be made in order to arrive at an accurate determination of paper strength. I have found that a satisfactory correction can be made by utilizing an additive factor which is a function of the difference between the forces applied to transducers 41A and 41C.

Complete empirical equations for determining directional paper strengths are as follows:

$$S_{md} = A \frac{L_a + L_c}{\bar{L}_a + \bar{L}_c} + (B x W^E x T^F) + C x V^D + G x (L_a - L_c)^H \quad (1)$$

$$S_{cd} = A \frac{L_b + L_d}{\bar{L}_b + \bar{L}_d} + (B x W^E x T^F) + C x V^D + G x (L_a - L_c)^H \quad (2)$$

Where
 $S_{md}$ is the machine direction strength of the paper;
 $S_{cd}$ is the cross direction strength of the paper;
 A, B, C, D, E, F, G and H are constants;
 $L_a$ through $L_d$ are the instantaneous forces applied to transducers 41A through 41D;
 $\bar{L}_a$ through $\bar{L}_d$ are the average forces applied to transducers 41A through 41D across the width of the paper;
 W is the basis weight of the paper;
 T is the thickness of the paper; and
 V is the velocity of the paper leaving the calender.

The above equations have been found to correlate well with both the standard tensile and the standard STFI tests for paper strength, both commonly used. The constants A through H vary depending on which test is being simulated. The last additive factor in each of the above equations represents the correction for web misalignment.

A modification of equations (1) and (2) allows the system to be used to determine the "Mullen" strength of the paper:

$$S_{mu} = A \frac{L_a + L_b + L_c + L_d}{\bar{L}_a + \bar{L}_b + \bar{L}_c + \bar{L}_d} + (B x W^E x T^F) + C x V^D + G x (L_a - L_c)^H \quad (3)$$

where
 $S_{mu}$ is the "Mullen" strength;
All other factors are the same as in equations (1) and (2).

The above equations have been found to be applicable to a wide variety of papers being manufactured. The constants A, b, C, D, E and F vary somewhat depending on the particular paper being made, and which test is being simulated, but generally fall within the following ranges (where basis weight is in pounds per 1000 square feet, thickness is in mils, and velocity is in feet per minute):
 A from 20 to 22
 B from 0.5 to 5
 C from 0 to 0.07
 D from 0.5 to 5
 E from 1 to 2
 F from −1 to +1

The constants G and H must be empirically determined since they are strongly dependent on the particular setup.

It may be noted that the terms of the above equations involving $L_a$ through $L_d$ are in the form of a ratio with $\bar{L}_a$ through $\bar{L}_d$. This indicates that "elastic modulus" is primarily an indicator of how strength varies across the width of the paper, while the average strength is primarily determined as a function of basis weight, thickness, and web velocity.

Machine rigidity is an important factor in maintaining accuracy of measurement. In particular, it is important that the lowest point on the periphery of wheel 29 be maintained at a constant distance below the top surface of ring 26. If the mechanical rigidity of the structure is such that the spacing cannot be maintained, sensing means can easily be adapted to sense the relative positions of wheel 29 and ring 26, and to apply a correction to the equation to account for variations. A conventional sensor for this purpose is shown diagrammatically in FIG. 2 identified by the numeral 39. The output of displacement sensor 39 is designated as "Z" and is used to modify the first term of the strength equation. For example, if equation (1) was in use, the first term of the equation would be:

$$f(Z) \times A \frac{L_a + L_c}{\bar{L}_a + \bar{L}_c}$$

where f(Z) is an empirical function of the output of sensor 39.

What has been described is a novel sensor and system for determining paper strength "on line". A presently preferred embodiment has been disclosed for purposes of illustration, but it will be understood that persons skilled in the art will be able to make changes thereto within the spirit of the invention.

For example, the presently preferred embodiment of the invention includes a segmented ring with four segments and four load cells, but that is not the only possible number of sheet supporting areas. It is possible to get meaningful information from even a single load cell coupled to one of the segments. As can be easily seen, many combinations are possible within the teachings of the above disclosure, therefore the scope of the invention should be limited only by the following claims.

I claim:

1. A sensor for sensing a physical characteristic of a moving sheet of material under tension which comprises:
    (a) support means for supporting one side of said sheet at a plurality of areas of the sheet disposed around an unsupported point, a first of said areas being spaced from the unsupported point on a line oriented in the machine direction of the sheet and a second of said areas being spaced from the unsupported point on a line oriented in the cross direction of the sheet;
    (b) deflecting means for pressing said sheet at the unsupported point so that the sheet is forced against said support means at both the first and second areas; and (c) a first load cell for sensing the force exerted by said sheet on the support means at the first area and a second load cell for sensing the force exerted by said sheet on the support means at the second area.

2. A sensor as recited in claim 1, wherein the sheet material is paper, the sensor further comprising a computer for determining the failure strength of the paper sheet based upon the sensed forces.

3. A sensor as recited in claim 2, further comprising: means for determining the basis weight of the paper; means for determining the thickness of the paper; and wherein the computer determines the sheet strength based upon the sensed forces, the basis weight and the thickness.

4. A sensor as recited in claim 2, further comprising means for scanning the support means and deflecting means in unison back and forth across the sheet, and wherein the computer computes the sheet strength at various locations across the sheet.

5. A sensor as recited in claim 1 where said means for pressing said sheet against said support means comprises a free running wheel pressing against said unsupported point.

6. A sensor as recited in claims 1 or 5 wherein the force sensed by each load cell acts in a direction approximately normal to the plane of the sheet.

7. A sensor as recited in claim 1, wherein the load cells provide signals indicative of the sensed forces, and the sensor further comprises a computer operatively coupled to the load cells for determining the failure strength of the sheet along at least one direction of the sheet based upon the signals.

8. A system for determining the failure strength of a moving sheet of paper which comprises:
   (a) means for determining the basis weight of said paper;
   (b) means for determining the thickness of said paper;
   (c) means for sensing a physical characteristic of said sheet of paper comprising:
      (i) support means for supporting said sheet at a plurality of areas disposed about an unsupported region of the sheet;
      (ii) means for pressing said sheet against said support means;
      (iii) a plurality of load cells operatively coupled to the support means, each for sensing the force exerted by said sheet against less than all of said areas;
   (d) means for moving said means for sensing a physical characteristics across the width of said moving sheet in a continuous scanning motion; and
   (e) a computer for determining the failure strength of said moving sheet of paper along a particular direction as a function of said basis weight, said thickness, and said physical characteristic, and providing an output indicative of the determined strength.

9. A system as recited in claim 8 wherein said function includes the terms:

$$S = A \times \frac{L_1 + L_2}{\overline{L}_1 + \overline{L}_2} + (B \times W^E \times T^F)$$

where
S is the strength of said paper,
A, B, E and F are constants,
$L_1$ and $L_2$ are the instantaneous forces applied to two of said load cells, said two load cells sensing force exerted on areas of said support means on opposite sides of said unsupported region,
$\overline{L}_1$ and $\overline{L}_2$ are the average forces applied to said two load cells over the width of said sheet,
W is the basis weight of said paper, and
T is the thickness of said paper.

10. A system as recited in claim 9, where, if W is stated in pounds per thousand square feet and T is stated in mils, A is between 20 and 33, B is between 0.5 and 5, E is between 1 and 2, and F is between −1 and +1.

11. A system as recited in claim 8 and further including means for sensing the velocity of said moving sheet of paper, said function for determining the strength of said moving sheet of paper further including said velocity of said moving sheet of paper.

12. A system as recited in claim 11 wherein said function includes the terms is:

$$S = A \times \frac{L_1 + L_2}{\overline{L}_1 + \overline{L}_2} + (B \times W^E \times T^F) + C \times V^D$$

where
S is the strength of said paper,
A, B, C, D, E and F are constants,
$L_1$ and $L_2$ are the instantaneous forces applied to two of said load cells, said two load cells sensing force exerted on areas of said support means on opposite sides of said unsupported region,
$\overline{L}_1$ and $\overline{L}_2$ are the average forces applied to said two load cells over the width of said sheet,
W is the basis weight of said paper,
T is the thickness of said paper, and
V is the velocity of said paper.

13. A system as recited in claim 12 where, if W is stated in pounds per thousand square feet, T is stated in mils, and V is stated in feet per minute, A is between 20 and 22, B is between 0.5 and 5, C is between 0 and 0.07, D is between 0.5 and 5, E is between 1 and 2, and F is between −1 and +1.

14. A system as recited in claims 8, 9, 10, 11, 12 or 13, further including:
   (a) means for sensing the relative displacement between said support means and said means for pressing said sheet against said support means, and for producing an output indicative of the sensed relative displacement; and
   (b) means for altering the output of said computer responsive to the output of said means for sensing said relative displacement.

15. A system as recited in claims 8, 9, 10, 11, 12, 13, or 14 where said means for pressing said sheet against said support means is a free running wheel pressed against said unsupported region.

16. A system as recited in claims 8, 9, 10, 11, 12, 13, or 14 and further including means for altering the output of said computer responsive to misalignment of said sheet with the surface of said support means.

17. A system as recited in claim 16 where said misalignment is sensed by sensing the difference in loads exerted on two of said areas located on opposite sides of said unsupported region in the direction of motion of said sheet.

18. A sensor for determining the failure strength of a sheet material, comprising:
   (a) a plurality of support means for supporting one side of the sheet against a deflecting force and defining an unsupported region between the support means, wherein a first of said support means is disposed adjacent to the unsupported region in a first direction from the unsupported region and a second of said support means is disposed adjacent to the unsupported region in a direction from the unsupported region other than said first direction;

(b) deflecting means providing the deflecting force for deflecting the sheet into the unsupported region so that the sheet presses against the plurality of support means;

(c) a first force sensor operatively coupled to the first support means for sensing the force of the sheet against the first support means and producing a first signal indicative of the sensed force; and (d) a computer for determining the failure strength of the sheet material along a line oriented in the first direction, said determination being based upon the first signal.

19. A sensor as recited in claim 18, wherein the sheet is moving in the first direction and the first and second support means are disposed on opposite sides of the unsupported region on said line oriented in the first direction.

20. A sensor as recited in claim 18, wherein the sheet is moving in a direction perpendicular to the first direction and the first and second support means are disposed on opposite sides of the unsupported region on said line oriented in the first direction.

21. A sensor recited in claim 18, wherein the second support means is disposed adjacent to the unsupported region in a direction perpendicular to the first direction, the sensor further including a second force sensor operatively coupled to the second support means for sensing the force of the sheet against the second support means and producing a second signal indicative of the sensed force, and wherein the computer further determines the failure strength of the sheet in the second direction based upon the second signal.

22. A sensor as recited in claim 21, wherein the material is a moving sheet of paper.

23. A sensor as recited in claim 18, wherein the sheet material is paper, the sensor further comprising scanning means for scanning the plurality of support means and deflecting means in unison back and forth across the sheet, and wherein the computer determines the sheet strength at various locations across the sheet.

24. A system for determining the cross direction and machine direction failure strengths of a paper sheet comprising:

(a) a sheet of paper having a first and second side, the sheet moving under tension in the plane of the sheet;

(b) a ring having four segments, wherein each of the four ring segments is in contact with the first side of said sheet, two segments on opposite sides of the ring being located on a line oriented in the machine direction of the sheet and two other segments being located on a line oriented in the cross direction of the sheet;

(c) a wheel rotatably contacting the second side of the sheet to deflect the moving paper into the center of the ring;

(d) a first load cell operatively coupled to one of the ring segments located in the cross direction for generating a signal indicative of the force of the sheet against said one ring segment;

(e) a second load cell operatively coupled to a second of the ring segments located in the machine direction for generating a signal indicative of the force of the sheet against the second ring segment; and (f) a computer for receiving the signals from the load cells and computing the cross direction sheet failure strength based upon the force signal from the first load cell and the machine direction sheet failure strength based upon the signal from the second load cell.

25. A sensor for sensing a physical characteristic of a moving sheet of material under tension, comprising:

(a) support means for supporting a side of said sheet at at least two areas of the sheet adjacent to an unsupported region of the sheet, said two areas being disposed on opposite sides of the unsupported region and in the cross directions from the unsupported region;

(b) deflecting means for pressing against said sheet in the unsupported region such that the sheet is forced against the support means; and (c) a force sensor for sensing the force exerted by said sheet on the support means at at least one of said areas disposed in the cross directions from the unsupported region.

26. A sensor as recited in claim 25, wherein the force sensor senses the force on less than all of said areas.

27. A process for determining the failure strength of a moving sheet of material, comprising the steps of:

(a) deflecting a portion of the moving sheet into an unsupported region between a plurality of sheet supports;

(b) sensing the force of the sheet against at least one of the sheet supports, which sheet supports are disposed adjacent to the unsupported region and on a line oriented in a predetermined direction passing through the deflected sheet portion; and (c) determining the sheet failure strength along the sheet directions defined by the lengthwise orientation of the line, where said strength determination is based upon the sensed force.

28. The process recited in claim 27, wherein the force of the sheet against the sheet supports disposed on a line oriented in the cross direction is sensed and the sheet strength in the cross direction is determined based upon the sensed force.

29. The process recited in claim 27, wherein the force of the sheet against the sheet supports disposed on a line oriented in the machine direction is sensed and the sheet strength in the machine direction is determined based upon the sensed force.

30. The process recited in claim 27, wherein the sheet material is paper.

31. The process recited in claim 30, wherein the moving sheet is deflected at different points across the sheet at different times and the strength of the sheet at each of said points is determined.

32. A sensor for sensing a physical characteristic of a moving sheet of material under tension which comprises:

(a) support means including a ring having a plurality of ring segments for supporting a side of said sheet at a plurality of areas disposed around an unsupported point, a first of said segments being spaced from the unsupported point on a line oriented in the machine direction of the sheet and a second of said segments being spaced from the unsupported point on a line oriented in the cross direction of the sheet, said ring having third and fourth ring segments located, respectively, on opposite sides of the unsupported point from the first and second segments;

(b) deflecting means for pressing said sheet at the unsupported point so that the sheet is forced against said support means; and (c) at least two load cells for sensing the force exerted by said sheet on ring segments located on opposite sides of the unsupported point.

33. A sensor as recited in claim 32, wherein said means for pressing the sheet against said support means comprises a free running wheel pressing against said unsupported point.

34. A sensor for sensing a physical characteristic of a moving sheet of material under tension which comprises:

(a) support means including a ring having a plurality of ring segments for supporting a side of said sheet at a plurality of areas disposed around an unsupported point, a first of said segments being spaced from the unsupported point on a line oriented in the machine direction of the sheet and a second of said segments being spaced from the unsupported point on a line oriented in the cross direction of the sheet, said ring having third and fourth ring segments located, respectively, on opposite sides of the unsupported point from the first and second segments;

(b) deflecting means for pressing said sheet at the unsupported point so that the sheet is forced against said support means; and (c) at least two pairs of load cells, the load cells in each of said pair of load cells sensing forces exerted by said sheet on ring segments located on opposite sides of the unsupported point.

35. A sensor as recited in claim 34, wherein said means for pressing the sheet against said support means comprises a free running wheel pressing against said unsupported point.

* * * * *

UNITED STATES PATENT AND TRADEMARK OFFICE
CERTIFICATE OF CORRECTION

PATENT NO. : 4,866,984

DATED : September 19, 1989

INVENTOR(S) : PAUL J. HOUGHTON

It is certified that error appears in the above-identified patent and that said Letters Patent is hereby corrected as shown below:

In the Abstract, line 1, --quality-- should replace "quantity".

The Drawing Sheet, consisting of figs. 3-5, should be added as shown on the attached page.

UNITED STATES PATENT AND TRADEMARK OFFICE
CERTIFICATE OF CORRECTION

PATENT NO. : 4,866,984
DATED : September 19, 1989
INVENTOR(S) : PAUL J. HOUGHTON It is certified that error appears in the above-identified patent and that said Letters Patent is hereby corrected as shown below:

Column 2, line 6, --D774-- should replace "D7774".

Column 3, line 34, the word --the-- should replace "and".

Column 4, line 44, the word --to-- should be inserted after the word "Referring".

Column 5, equation (1) should read as follows:

$$S_{md} = A \; \frac{L_a + L_c}{\overline{L}_a + \overline{L}_c} + (B x W^E x T^F) + C x V^D + G x (L_a - L_c)^H \tag{1}$$

Column 5, equation (2) should read as follows:

$$S_{cd} = A \; \frac{L_b + L_d}{\overline{L}_b + \overline{L}_d} + (B x W^E x T^F) + C x V^D + G x (L_a - L_c)^H \tag{2}$$

Column 5, equation (3) should read as follows:

$$S_{mu} = A \; \frac{L_a + L_b + L_c + L_d}{\overline{L}_a + \overline{L}_b + \overline{L}_c + \overline{L}_d} + (B x W^E x T^F) + C x V^D + G x (L_a - L_c)^H \tag{3}$$

Column 6, line 34, the equation should read as follows:

$$f(Z) x A \; \frac{L_a + L_c}{\overline{L}_a + \overline{L}_c}$$

UNITED STATES PATENT AND TRADEMARK OFFICE
CERTIFICATE OF CORRECTION

PATENT NO. : 4,866,984

DATED : September 19, 1989

INVENTOR(S) : PAUL J. HOUGHTON

It is certified that error appears in the above-identified patent and that said Letters Patent is hereby corrected as shown below:

IN THE CLAIMS:

Column 7, claim 9, line 61, the equation should read as follows:

$$S = A \times \frac{L_1 + L_2}{\overline{L}_1 + \overline{L}_2} + (B \times W^E \times T^F)$$

Column 8, claim 12, line 17, "is" should be deleted.

Column 8, claim 12, line 20, the equation should read as follows:

$$S = A \times \frac{L_1 + L_2}{\overline{L}_1 + \overline{L}_2} + (B \times W^E \times T^F) + C \times V^D$$

Signed and Sealed this

Twelfth Day of January, 1993

Attest:

DOUGLAS B. COMER

*Attesting Officer*     *Acting Commissioner of Patents and Trademarks*